(12) United States Patent
Korkuch et al.

(10) Patent No.: US 9,808,598 B2
(45) Date of Patent: Nov. 7, 2017

(54) FLEXIBLE TIP DILATOR

(71) Applicant: TELEFLEX MEDICAL INCORPORATED, Morrisville, NC (US)

(72) Inventors: Christopher N. Korkuch, Chester Springs, PA (US); Allen R. Mantz, New Ringgold, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 0 days.

(21) Appl. No.: 14/944,121

(22) Filed: Nov. 17, 2015

(65) Prior Publication Data

US 2016/0220795 A1    Aug. 4, 2016

Related U.S. Application Data

(60) Provisional application No. 62/111,664, filed on Feb. 4, 2015.

(51) Int. Cl.
*A61M 25/00* (2006.01)
*A61M 29/00* (2006.01)
*A61M 25/06* (2006.01)

(52) U.S. Cl.
CPC ...... *A61M 25/0068* (2013.01); *A61M 25/001* (2013.01); *A61M 25/008* (2013.01); *A61M 25/0045* (2013.01); *A61M 25/0069* (2013.01); *A61M 25/0662* (2013.01); *A61M 29/00* (2013.01); *A61M 2025/0081* (2013.01)

(58) Field of Classification Search
CPC ........ A61M 25/001; A61M 2025/0081; A61M 29/00; A61M 25/0069; A61M 25/0068; A61M 2029/025; A61M 29/02; A61B 2017/320044; A61B 2017/00292; A61B 2017/1205; A61B 2017/12054; A61B 2017/12095; A61B 2017/1209; A61B 2017/12086; A61B 2017/12081; A61B 2017/12068; A61B 2017/12063; A61B 2017/12059
USPC ......... 604/523, 164; 600/433, 434, 435, 585
See application file for complete search history.

(56) References Cited

U.S. PATENT DOCUMENTS

| | | |
|---|---|---|
| 3,877,429 A | 4/1975 | Rasumoff |
| 4,451,256 A | 5/1984 | Weikl et al. |
| 4,705,041 A | 11/1987 | Kim |
| 4,863,442 A | 9/1989 | DeMello et al. |
| 4,906,241 A | 3/1990 | Noddin et al. |
| 4,950,257 A | 8/1990 | Hibbs et al. |
| 4,963,313 A | 10/1990 | Noddin et al. |
| 4,969,875 A | 11/1990 | Ichikawa |

(Continued)

FOREIGN PATENT DOCUMENTS

WO    WO2009070682 A1    6/2009

*Primary Examiner* — Nathan R Price
*Assistant Examiner* — John Doubrava
(74) *Attorney, Agent, or Firm* — Baker & Hostetler LLP

(57) ABSTRACT

A flexible tip dilator is disclosed. The flexible tip dilator includes a hollow elongated tubular member with a proximal region and a tapered distal region. The tapered distal region has three regions with a first region made from at least a first material but not a second material and a third region made from at least the second material but not the first material. The second region is includes both the first and second materials overlapping one another.

10 Claims, 3 Drawing Sheets

(56) References Cited

U.S. PATENT DOCUMENTS

| | | |
|---|---|---|
| 4,976,690 A | 12/1990 | Solar et al. |
| 4,998,923 A | 3/1991 | Samson et al. |
| 5,011,478 A | 4/1991 | Cope |
| 5,074,846 A | 12/1991 | Clegg et al. |
| 5,167,627 A | 12/1992 | Clegg et al. |
| 5,205,830 A | 4/1993 | Dassa et al. |
| 5,242,394 A | 9/1993 | Tremulis |
| 5,292,311 A | 3/1994 | Cope |
| 5,300,032 A | 4/1994 | Hibbs et al. |
| 5,395,341 A | 3/1995 | Slater |
| 5,449,343 A | 9/1995 | Samson et al. |
| 5,499,975 A | 3/1996 | Cope et al. |
| 5,507,751 A | 4/1996 | Goode et al. |
| 5,527,282 A | 6/1996 | Segal |
| 5,533,985 A * | 7/1996 | Wang ............... A61M 25/0009 600/433 |
| 5,558,643 A | 9/1996 | Samson et al. |
| 5,643,209 A | 7/1997 | Fugoso et al. |
| 5,669,881 A | 9/1997 | Dunshee |
| 5,685,856 A | 11/1997 | Lehrer |
| 5,695,469 A | 12/1997 | Segal |
| 5,755,708 A | 5/1998 | Segal |
| 5,823,995 A | 10/1998 | Fitzmaurice et al. |
| 5,827,225 A | 10/1998 | Ma Schwab |
| 5,827,231 A | 10/1998 | Harada |
| 5,885,258 A | 3/1999 | Sachdeva et al. |
| 5,944,732 A | 8/1999 | Raulerson et al. |
| 6,004,341 A | 12/1999 | Zhu et al. |
| 6,053,904 A | 4/2000 | Scribner et al. |
| 6,059,752 A | 5/2000 | Segal |
| 6,066,114 A | 5/2000 | Goodin et al. |
| 6,106,540 A * | 8/2000 | White ............... A61M 25/0662 606/185 |
| 6,156,054 A | 12/2000 | Zadno-Azizi et al. |
| 6,206,822 B1 | 3/2001 | Foley et al. |
| 6,245,054 B1 | 6/2001 | Fuimaono et al. |
| 6,334,863 B1 | 1/2002 | Srinivasan |
| 6,361,529 B1 | 3/2002 | Goodin et al. |
| 6,368,302 B1 | 4/2002 | Fitzmaurice et al. |
| 6,379,372 B1 | 4/2002 | Dehdashtian et al. |
| 6,488,662 B2 | 12/2002 | Sirimanne |
| 6,637,435 B2 | 10/2003 | Ciaglia et al. |
| 6,641,564 B1 | 11/2003 | Kraus |
| 6,692,462 B2 | 2/2004 | Mackenzie et al. |
| 6,780,175 B1 | 8/2004 | Sachdeva et al. |
| 6,887,192 B1 | 5/2005 | Whayne et al. |
| 6,905,481 B2 | 6/2005 | Sirimanne |
| 6,916,330 B2 | 7/2005 | Simonson |
| 6,997,900 B2 | 2/2006 | Weststrate et al. |
| 7,001,396 B2 | 2/2006 | Glazier et al. |
| 7,008,431 B2 | 3/2006 | Simonson |
| 7,037,321 B2 | 5/2006 | Sachdeva et al. |
| 7,074,226 B2 | 7/2006 | Roehm, III et al. |
| 7,166,088 B2 | 1/2007 | Heuser |
| 7,306,574 B2 | 12/2007 | Massey et al. |
| 7,309,344 B2 | 12/2007 | Bakos et al. |
| 7,549,975 B2 | 6/2009 | Lee et al. |
| 7,578,801 B2 | 8/2009 | Weststrate et al. |
| 7,618,430 B2 | 11/2009 | Scheib |
| 7,618,431 B2 | 11/2009 | Roehm, III et al. |
| 7,655,021 B2 | 2/2010 | Brasington et al. |
| 7,686,603 B2 | 3/2010 | Fairy |
| 7,717,951 B2 | 5/2010 | Flagle et al. |
| 7,727,251 B2 | 6/2010 | Spurchise et al. |
| 7,731,707 B2 | 6/2010 | Heller et al. |
| 7,815,608 B2 | 10/2010 | Schafersman et al. |
| 7,824,410 B2 | 11/2010 | Simonson et al. |
| 8,025,647 B2 | 9/2011 | Siess et al. |
| 8,052,670 B2 | 11/2011 | Sachdeva et al. |
| 8,066,674 B2 | 11/2011 | Heuser |
| 8,105,286 B2 | 1/2012 | Anderson et al. |
| 8,109,908 B1 | 2/2012 | Kraus |
| 8,152,829 B2 | 4/2012 | Scheib |
| 8,192,402 B2 | 6/2012 | Anderson et al. |
| 8,192,437 B2 | 6/2012 | Simonson |
| 8,202,251 B2 | 6/2012 | Bierman et al. |
| 8,202,289 B2 | 6/2012 | Woo |
| 8,235,999 B2 | 8/2012 | Simonson |
| 8,340,779 B2 | 12/2012 | Harris et al. |
| 8,361,151 B2 | 1/2013 | Simonson |
| 8,377,037 B2 | 2/2013 | Sachdeva et al. |
| 8,386,052 B2 | 2/2013 | Harris et al. |
| 8,394,135 B2 | 3/2013 | Jensen et al. |
| 8,444,678 B2 | 5/2013 | Simonson et al. |
| 8,444,802 B2 | 5/2013 | Lee et al. |
| 8,460,331 B2 | 6/2013 | Chin |
| 8,491,620 B2 | 7/2013 | Brasington et al. |
| 8,540,674 B2 | 9/2013 | Kassab et al. |
| 8,556,905 B2 | 10/2013 | Simonson |
| 8,562,573 B1 | 10/2013 | Fischell |
| 8,568,436 B2 | 10/2013 | Ciaglia et al. |
| 8,579,805 B2 * | 11/2013 | Accisano, III ...... A61M 25/001 600/184 |
| 8,641,717 B2 | 2/2014 | Defossez et al. |
| 8,709,064 B2 | 4/2014 | Rasmussen et al. |
| 8,747,428 B2 | 6/2014 | Fischell et al. |
| 8,759,805 B2 | 6/2014 | Lambert et al. |
| 2002/0035373 A1 | 3/2002 | Carlson et al. |
| 2002/0045855 A1 | 4/2002 | Frassica |
| 2004/0092879 A1 | 5/2004 | Kraus et al. |
| 2005/0004593 A1 | 1/2005 | Simonson |
| 2005/0049663 A1 | 3/2005 | Harris et al. |
| 2005/0070949 A1 | 3/2005 | Bakos et al. |
| 2005/0245958 A1 | 11/2005 | Carlson et al. |
| 2006/0030872 A1 | 2/2006 | Culbert et al. |
| 2006/0047296 A1 | 3/2006 | Embry et al. |
| 2007/0106233 A1 | 5/2007 | Huang et al. |
| 2007/0185522 A1 | 8/2007 | Davies et al. |
| 2008/0243169 A1 | 10/2008 | Carlson et al. |
| 2009/0024089 A1 | 1/2009 | Levine et al. |
| 2009/0054872 A1* | 2/2009 | Magnuson .......... A61M 25/001 604/523 |
| 2009/0137870 A1 | 5/2009 | Bakos et al. |
| 2009/0149857 A1 | 6/2009 | Culbert et al. |
| 2009/0163890 A1 | 6/2009 | Clifford et al. |
| 2009/0199849 A1 | 8/2009 | Enk |
| 2009/0281386 A1 | 11/2009 | Acosta et al. |
| 2009/0312786 A1 | 12/2009 | Trask et al. |
| 2009/0318896 A1 | 12/2009 | Weststrate et al. |
| 2010/0010530 A1 | 1/2010 | Rhee |
| 2010/0198191 A1 | 8/2010 | Clifford et al. |
| 2010/0268244 A1 | 10/2010 | Hansen et al. |
| 2010/0274188 A1 | 10/2010 | Chang et al. |
| 2011/0021994 A1 | 1/2011 | Anderson et al. |
| 2011/0060182 A1 | 3/2011 | Kassab et al. |
| 2011/0137403 A1 | 6/2011 | Rasmussen et al. |
| 2011/0202006 A1 | 8/2011 | Bierman et al. |
| 2011/0270192 A1 | 11/2011 | Anderson et al. |
| 2012/0041536 A1 | 2/2012 | Hansen |
| 2012/0109056 A1 | 5/2012 | Rasmussen |
| 2012/0179102 A1 | 7/2012 | Blanchard et al. |
| 2012/0220942 A1 | 8/2012 | Hall et al. |
| 2012/0283640 A1 | 11/2012 | Anderson et al. |
| 2013/0123704 A1 | 5/2013 | Bierman et al. |
| 2013/0158414 A1 | 6/2013 | Sachdeva et al. |
| 2013/0158564 A1 | 6/2013 | Harris et al. |
| 2013/0184568 A1 | 7/2013 | Muni et al. |
| 2013/0184736 A1 | 7/2013 | Aman et al. |
| 2013/0245382 A1 | 9/2013 | Simonson et al. |
| 2013/0317438 A1 | 11/2013 | Ellingwood et al. |
| 2013/0317439 A1 | 11/2013 | Ellingwood et al. |
| 2014/0012231 A1 | 1/2014 | Fischell |
| 2014/0025038 A1 | 1/2014 | Kassab et al. |
| 2014/0039540 A1 | 2/2014 | Park |
| 2014/0051931 A1 | 2/2014 | Simonson |
| 2014/0081210 A1 | 3/2014 | Bierman et al. |
| 2014/0081241 A1 | 3/2014 | Accisano |
| 2014/0114291 A1 | 4/2014 | Defossez et al. |

* cited by examiner

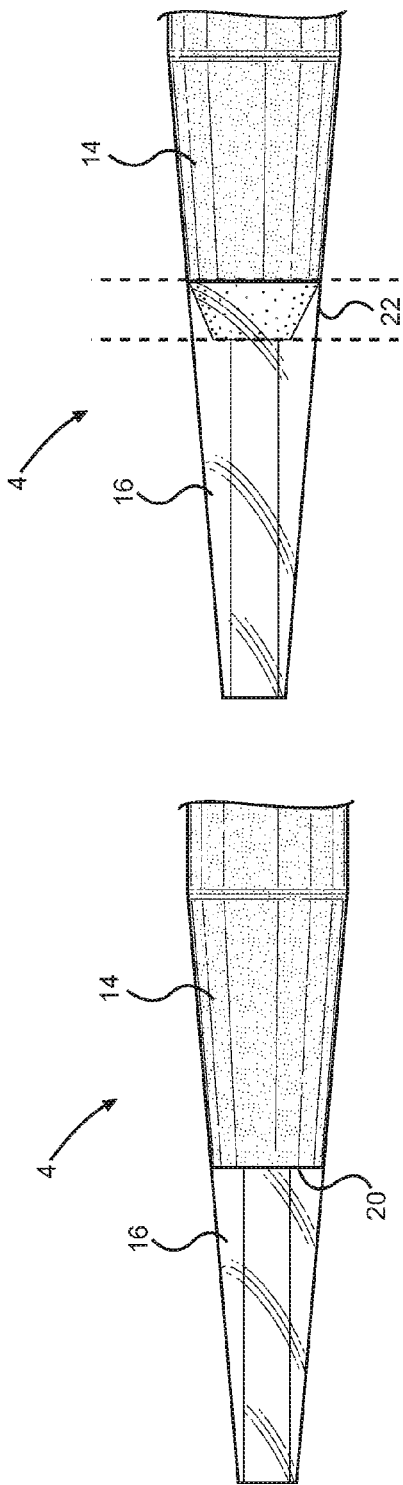
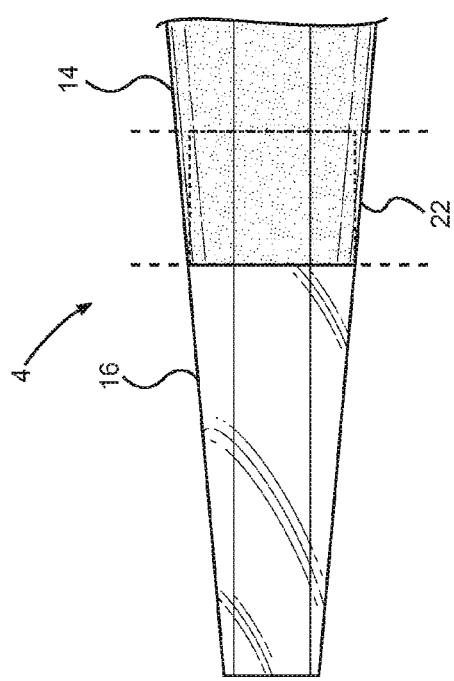
FIG. 3a
FIG. 3b
FIG. 3c

FLEXIBLE TIP DILATOR

CROSS-REFERENCE TO RELATED APPLICATIONS

This application claims priority to U.S. Provisional Patent App. No. 62/111,664, filed Feb. 4, 2015, the disclosure of which is hereby incorporated by reference in its entirety.

FIELD OF THE DISCLOSURE

The disclosure generally relates to a dilator. Specifically, the disclosure relates to a dilator having a flexible tip.

BACKGROUND

Dilators are generally used to stretch a channel created by a needle through the skin and subcutaneous tissue in a procedure to gain vascular access. In Internal Jugular insertions, dilators are inserted over a guidewire and, therefore, have a tip that tapers from a small diameter that is slightly greater than the diameter of the guidewire to the widest diameter of the dilator.

Dilators are traditionally made of polyethylene to achieve optimal product performance. The distal tips of the dilators are typically made of the same material as the rest of the dilator and are, therefore, stiff and sharp. Due to manufacturing variations and the need for minimized drag along the guidewire, dilator tips are usually loose around the guidewire, causing the dilator tip to catch tissue or damage vessel walls during dilation. In addition, due to their stiffness, the dilator tips cannot flex enough when there is tight bend over a short distance, causing a kink in the guidewire. Furthermore, dilator tips typically flare when the dilator hits an object like skin, subcutaneous tissue, or a vessel wall, causing sharp edges at the distal tip that can prevent insertion of the dilator or can damage a vessel during insertion.

Accordingly, there is a need for a dilator having a flexible tip such that risk of injury to vessels is reduced.

SUMMARY OF THE DISCLOSURE

The foregoing needs are met, to a great extent, by a flexible tip dilator. In one or more aspects, the flexible tip dilator is made of at least a first material and a second material. The flexible tip dilator includes a hollow elongated tubular member having a proximal region and a tapered distal region. The tapered distal region includes a first region, a second region distal to the first region, and a third region distal to the second region. The first region of the tapered distal region is made of at least the first material but not the second material. The second region of the tapered distal region includes the first material and a second material overlapping one another. The third region of the tapered distal region is made of at least the second material but not the first material. The second material is different from and more flexible relative to the first material.

In some aspects, the first region can have a first taper angle and the second region can have a second taper angle continuous with the first taper angle. In some aspects, the first material can be adhered over the second material in the second region, while in other aspects, the second material can be adhered over the first material in the second region. The first material can be polyethylene, polypropylene, polymethylpentene, fluoropolymer, polybutene-1, or a copolymer thereof. The second material can be ethyl-vinyl acetate, styrenic block co-polymers, or other thermoplastic elastomers. The second material can preferably be ethyl-vinyl acetate.

In some aspects, the elongated tubular member can have an inner diameter larger than an outer diameter of a guidewire. The proximal region of the hollow elongated tubular member can include a hollow hub.

Certain aspects of the flexible tip dilator have thus been outlined in order that the detailed description may be better understood. There are, of course, additional aspects of the disclosure that will be described below and which will form the subject matter of the claims.

In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the disclosure are illustrated by way of examples in the accompanying drawings.

FIG. 3a is a first partial cross-sectional view of the distal region of one aspect of a flexible tip dilator.

FIG. 3b is a second partial cross-sectional view of the distal region of another aspect of a flexible tip dilator.

FIG. 3c is a third partial cross-sectional view of the distal region of yet another aspect of a flexible tip dilator.

Aspects of the flexible tip dilator are described with reference to the drawings, in which like reference numerals refer to like parts throughout.

DETAILED DESCRIPTION

The flexible tip dilator disclosed herein minimizes vessel damage due to its tapered tip made from a flexible material, and provides improved tracking over the guidewire. In addition, insertion forces required to introduce the dilator into the vessel can be reduced.

Figure 1:
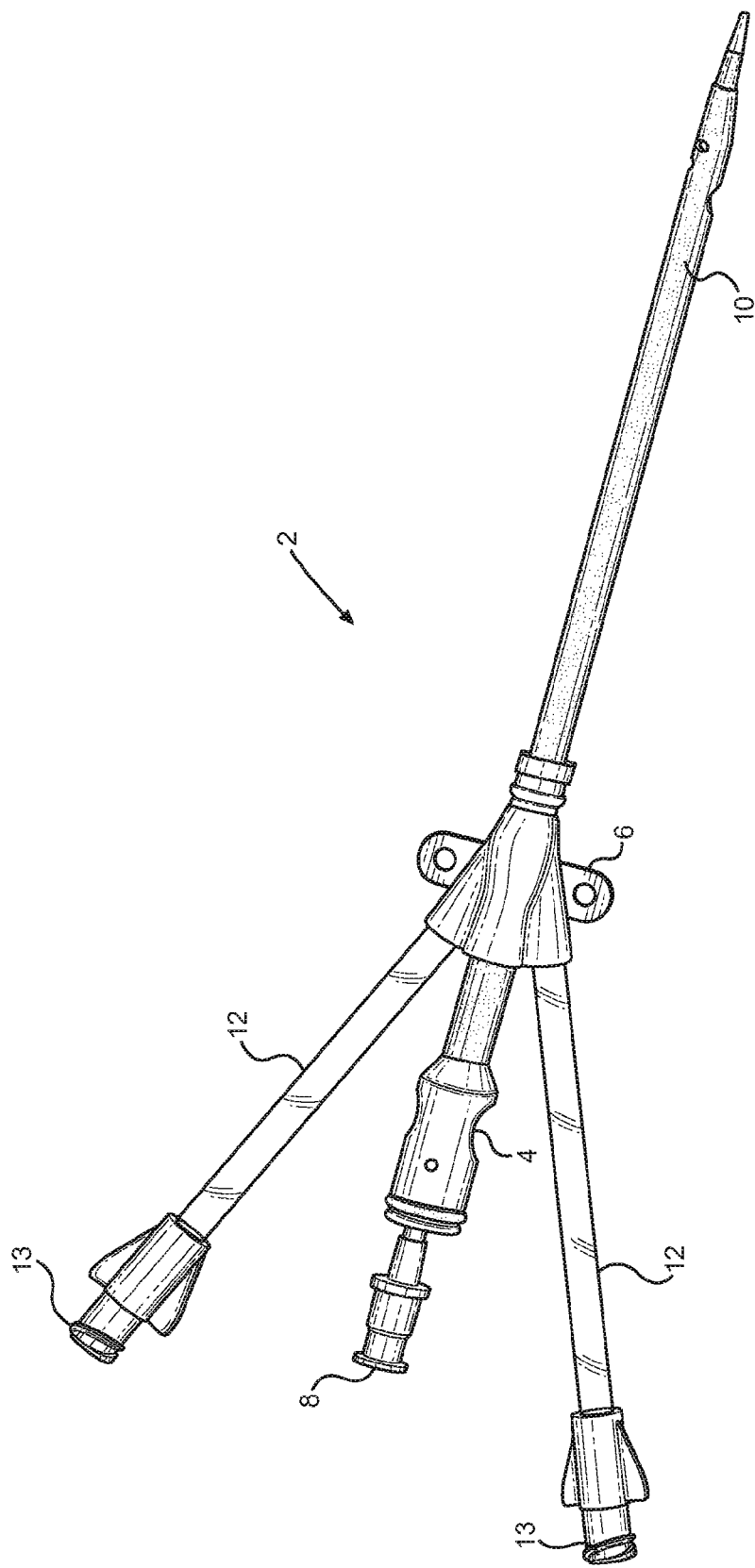
FIG. 1 is a perspective view of a dilator and sheath assembly.

Referring to FIG. 1, a dilator assembly 2 is illustrated. The dilator assembly 2 includes a dilator 4 and an introducer 10. The introducer 10 may be a cylindrical shaft with an end that may be tapered. An introducer hub 6 is located at the proximal end of the introducer. The dilator assembly 2 includes lumens 12 for injection and aspiration and hubs 13 at the proximal ends of the lumens 12.

The dilator 4 is an elongated tubular shaft having a hollow inner portion. The dilator 4 has a tapered distal end and a dilator hub 8 at its proximal end. The dilator 4 has an outer diameter smaller than an inner diameter of the introducer 10, such that the dilator 4 may be inserted into the proximal end of the introducer through the introducer hub 6. The dilator 4 and the dilator hub 8 may be fixed securely to one another in a manner that prevents axial and rotational movement of the dilator relative to the dilator hub 8.

Figure 2:
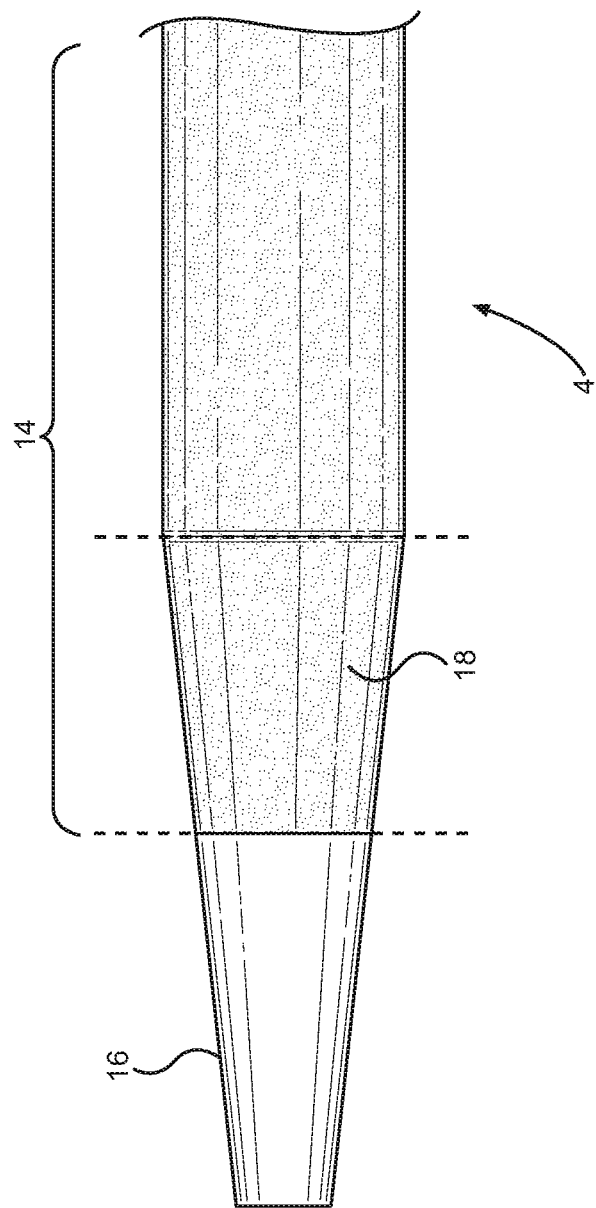
FIG. 2 is a side view of a distal region of one aspect of a flexible tip dilator.

One aspect of the distal region of the dilator 4 is illustrated in FIG. 2. The distal region of the dilator 4 includes two sections. A first region 14 includes a first material and the second region 16 includes a different second material more materially flexible than the first material. The first region 14 of the dilator 4 proximal of the tapered region 18 does not include the second material. The second region 16 of the dilator 4 does not include the first material. The dilator 4 may also begin tapering at a tapered region 18 of the first region 14 and continue tapering through the second region 16. The tapered region 18 may begin at any point along the length of the dilator 4. Alternatively, the tapered region 18 may also extend along the full length of the dilator 4. The inner diameter of the dilator 4 may be large enough to accommodate a guidewire having a diameter between, for example, 0.01 to 0.05 inches.

In some aspects, the first region 14 may be made from a polyolefin, such as high density polyethylene (HDPE) or low density polyethylene (LDPE). The first region 14 may alternatively be made of polypropylene, fluoropolymer, polymethylpentene, polybutene-1, or a copolymer thereof, or another polymer having similar stiffness properties. The selected polymer may exhibit crazing as opposed to cracking when reaching material yield. The first region 14 may have a low coefficient of friction, be hydrophobic, and/or have low surface energy.

In some aspects, the second region 16 may be made of ethylene-vinyl acetate (EVA) or another elastomeric polymer such as styrenic block copolymers, or other thermoplastic elastomers. The second region 16 may have a Shore durometer measurement less than a Shore durometer measurement of the first region 14 and have a high strain before failure and/or relatively high tear resistance. The material of the second region 16 may adhere to the material of the first region 14 during a melting process.

FIGS. 3a-3c describe different aspects of the distal tip of the dilator 4. In FIG. 3a, the first region 14 may contact the second region 16 along an even seam 20 at an annular cross-section. The first region 14 may adhere to the second region 16 at seam 20 after a melting process or using an adhesive. Alternatively, as shown in FIG. 3b, the second region 16 may adhere over the first region 14 in an overlap region 22. Due to the increased surface area of contact between the first region 14 and the second region 16 relative to the aspect shown in FIG. 3a, there may be improved adhesion between the first region 14 and the second region 16 in the aspect shown in FIG. 3b. In addition, because the second region 16 may adhere over the first region 14, there may be a less likelihood that a corner of the first region 14 catches onto a vessel during insertion of the dilator 4.

In yet another aspect, as shown in FIG. 3c, the first region 14 may adhere over the second region 16 in an overlap region 22. Due to the increased surface area of contact between the first region 14 and the second region 16 relative to the aspect shown in FIG. 3a, there may also be improvement in adhesion between the first region 14 and the second region 16 in the aspect shown in FIG. 3c. Because of the material and structural properties of the first region 14 and the second region 16, this configuration may provide improved mechanical support for material adhesion between the two regions through a friction fit or an interference fit.

The many features and advantages of the flexible tip dilator 4 are apparent from the detailed specification, and thus, the claims cover all such features and advantages within the scope of this application. Further, numerous modifications and variations are possible. As such, it is not desired to limit the flexible tip dilator 4 to the exact construction and operation described and illustrated and, accordingly, all suitable modifications and equivalents may fall within the scope of the claims.

What is claimed is:

1. A flexible tip dilator made of at least a first material and a second material, the flexible tip dilator comprising:
   a hollow elongated tubular member comprising a proximal region and a tapered distal region, the tapered distal region being of continuously decreasing diameter and defining an exterior surface of the flexible tip dilator, the tapered distal region comprising a first region, a second region distal to the first region, and a third region distal to the second region,
   wherein the first region of the tapered distal region is made of at least the first material but not the second material,
   wherein the second region of the tapered distal region comprises the first material and the second material overlapping one another, the second material being different from and more flexible relative to the first material, and
   wherein the third region of the tapered distal region is made of at least the second material but not the first material,
   wherein the first material in at least the first region of the tapered distal region forms a first portion of the exterior surface of the flexible tip dilator,
   wherein the second material in at least the third region of the tapered distal region forms a second portion of the exterior surface of the flexible tip dilator.

2. The flexible tip dilator of claim 1, wherein the first region has a first taper angle.

3. The flexible tip dilator of claim 2, wherein the second region has a second taper angle continuous with the first taper angle.

4. The flexible tip dilator of claim 1, wherein the first material is adhered over the second material in the second region.

5. The flexible tip dilator of claim 1, wherein the second material is adhered over the first material in the second region.

6. The flexible tip dilator of claim 1, wherein the hollow elongated tubular member has an inner diameter larger than an outer diameter of a guidewire.

7. The flexible tip dilator of claim 1, wherein the first material is selected from the group consisting of polyethylene, polypropylene, fluoropolymer, polymethylpentene, polybutene-1, and a copolymer thereof.

8. The flexible tip dilator of claim 1, wherein the second material is selected from the group consisting of ethyl-vinyl acetate, styrenic block copolymers, or other thermoplastic elastomers.

9. The flexible tip dilator of claim 1, wherein the second material is ethyl-vinyl acetate.

10. The flexible tip dilator of claim 1, wherein the proximal region of the hollow elongated tubular member comprises a hollow hub.

* * * * *